US007877829B2

(12) United States Patent  (10) Patent No.: US 7,877,829 B2
Gonzalez et al.  (45) Date of Patent: Feb. 1, 2011

(54) SYSTEM AND METHOD FOR MAINTAINING AIR INFLATABLE MATTRESS CONFIGURATION

(75) Inventors: Juan L. Gonzalez, San Antonio, TX (US); Michael R. Oliva, San Antonio, TX (US); Kevin W. Bendele, Cibolo, TX (US); Bruce L. Phillips, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 12/117,291

(22) Filed: May 8, 2008

(65) Prior Publication Data

US 2008/0216248 A1  Sep. 11, 2008

Related U.S. Application Data

(62) Division of application No. 11/355,679, filed on Feb. 15, 2006, now Pat. No. 7,444,704.

(60) Provisional application No. 60/653,303, filed on Feb. 16, 2005.

(51) Int. Cl.
 *A61G 7/05* (2006.01)
(52) U.S. Cl. .................................. 5/713; 5/710; 5/655.3
(58) Field of Classification Search ...................... 5/600, 5/611, 713, 710, 655.3, 706, 654
See application file for complete search history.

(56) References Cited

U.S. PATENT DOCUMENTS

| 4,745,647 | A |   | 5/1988  | Goodwin |       |
|-----------|---|---|---------|---------|-------|
| 5,630,238 | A | * | 5/1997  | Weismiller et al. | 5/600 |
| 5,815,864 | A |   | 10/1998 | Sloop |       |
| 6,145,142 | A |   | 11/2000 | Rechin et al. |   |
| 6,524,239 | B1 |  | 2/2003  | Reed et al. | 600/300 |
| 6,560,804 | B2 | * | 5/2003  | Wise et al. | 5/713 |

(Continued)

OTHER PUBLICATIONS

Office Communication, issued in Chinese Patent Application No. 2006800051149, dated Oct. 23, 2009. (English Translation).

*Primary Examiner*—Fredrick Conley

(57) ABSTRACT

A system and method for maintaining an air inflation mattress configuration sufficient for patient support and comfort. Infrared illumination levels are measured within individual or groups of inflated mattress chambers. A staggered approach to illumination monitoring of chambers or sections to eliminate crosstalk between the infrared sensors is carried out. Distributed microprocessor controllers established in a network configuration utilizing controller network protocols reduces the wiring and connections necessary for the assembled system. Various mattress cushion construction techniques, such as sewing and or RF welding methods, are used for the creation of individual chambers utilizing specific types of IR translucent, transparent or reflective materials. The construction of the cushions and bladders in the system includes the use of various types of fabrics with low to high air loss qualities as required. The overall mattress assembly, including the control systems and the methodologies associated with such control systems, provide a unique approach to the maintenance of a consistently comfortable patient support surface. The use of a handheld unit for both programming the system and downloading information about the operation of the system is also anticipated. The specific cushion construction designs associated with the head, body, and foot cushion components of the mattress are tailored to operate specifically with the control capabilities (sensors and air flow regulators) of the invention.

7 Claims, 15 Drawing Sheets

U.S. PATENT DOCUMENTS

| | | |
|---|---|---|
| 6,892,405 B1 | 5/2005 | Dimitriu et al. |
| 6,904,631 B2 | 6/2005 | Vrzalik et al. |
| 6,928,681 B1 | 8/2005 | Stacy |
| 2004/0054821 A1 * | 3/2004 | Warren et al. .................. 710/8 |

* cited by examiner

SYSTEM AND METHOD FOR MAINTAINING AIR INFLATABLE MATTRESS CONFIGURATION

CROSS-REFERENCE TO RELATED APPLICATION

This application is a divisional of currently U.S. application Ser. No. 11/355,679 filed Feb. 15, 2006, which claims the benefit of U.S. provisional Application No. 60/653,303, filed Feb. 16, 2005, the entire disclosures of which are each incorporated herein by reference.

BACKGROUND OF THE INVENTION

1. Field of the Invention

The present invention relates generally to therapeutic beds and mattress systems and methods for maintaining their function. The present invention relates more specifically to improved systems and methods for controlling the configuration and characteristics of an inflatable air mattress utilizing an array of networked sensors and control modules.

2. Description of the Related Art

A number of problems are associated with inflatable air mattresses used in medical settings. Some such air mattresses are designed for therapeutic use and include high and low air loss fabric enclosures as well as control systems that alter the air pressure within the mattress in order to help reduce the occurrence of bed sores and similar detrimental effects of a long term bedridden condition. While in general air mattresses must be sufficiently firm to support a patient, they must also be sufficiently soft and resilient so as to be comfortable for the patient. Likewise, when therapeutic variations in the pressure within the air mattress are implemented, it is often difficult to maintain the elevation of the patient off a mattress base over the entire surface of the mattress. If, for whatever reason, the patient makes contact through the mattress surface with the more rigid mattress base, the result is the undesirable and uncomfortable occurrence that is referred to as "bottoming".

Control systems designed to maintain the inflation of therapeutic mattresses and the like must take into account significant variations in the force that a patient may exert on any single point in the mattress surface in addition to the overall force exerted by the weight of the patient across the mattress surface as an average. Point forces are generally experienced when a patient enters or exits the bed and directs their hands or feet, elbows or knees, into the mattress at a single localized point. In general, control systems that rely strictly on measurements of the pressure within an inflatable mattress fail to prevent the "bottoming" of the patient under a number of situations.

Some efforts to address the maintenance of mattress configuration involve the use of an increasing number of individual inflatable cells; any one of which may experience a large localized force, but with adjoining cells that would support the patient and prevent the "bottoming" from occurring. The problem with mattresses that utilize increased numbers of individual cells is that each cell must be individually connected to the inflation system and individually monitored by whatever control electronics might be put in place. Such mattresses would typically have extensive and quite complex air and electrical conduits running down and through the length of the mattress that individually address each of the inflation and control systems associated with the inflatable platform. The size, expense, complexity, and maintenance of such systems all become significant.

U.S. Pat. No. 6,560,804 issued to Wise et al. entitled System and Methods for Mattress Control in Relation to Patient Distance (Assignee KCI Licensing, Inc.) describes a system and method for detecting and monitoring the distance between a patient and a reference point on an inflatable air mattress and for controlling the air supply based upon changes in such distance. The devices for monitoring the patient distance include a heterodyning proximity detector, a force responsive distance sensing device, and a light responsive sensing device. The disclosure of U.S. Pat. No. 6,560,804 is incorporated herein in its entirety by reference.

Various other efforts have been made in the field to maintain the inflation of an air inflatable mattress at a particular height in order to maintain patient comfort.

SUMMARY OF THE INVENTION

The system of the present invention incorporates a number of unique system features and individual elements that together provide an overall system and method for maintaining an air inflation mattress configuration sufficient for patient support and comfort. While the overall system of the present invention is unique, there are additional individual components, elements, and methodologies associated with the system that are likewise unique and solve certain problems found in the prior art. In general, the disclosure that follows will focus on the following unique features and elements in the invention:

(1) The use of infrared illumination within individual chambers or groups of chambers.

(2) The staggered illumination and monitoring of alternating chambers or sections to reduce crosstalk between the infrared sensors.

(3) The use of distributed microprocessor controllers established on a network configuration utilizing network protocols in order to reduce the wiring and connections necessary for the assembled system.

(4) The use of various cushion and bladder construction techniques such as sewing and/or RF welding methods for the creation of individual chambers utilizing specific types of IR translucent, transparent, or reflective materials.

(5) The use of certain Gortex® type fabrics with low air loss qualities in the construction of various components within the mattress system.

(6) The overall mattress assembly, including the control systems and the methodologies associated with such control systems and its overall ability to improve the maintenance of an appropriate inflation profile.

(7) The use of a handheld wireless communication unit for uploading and downloading data, programming the system, and downloading information about the operation of the system.

(8) Specific cushion construction designs associated with the head, body, and foot cushion components of the mattress that facilitate the operation of the sensor and controller components of the system.

DETAILED DESCRIPTION OF THE PREFERRED EMBODIMENTS

Figure 1:
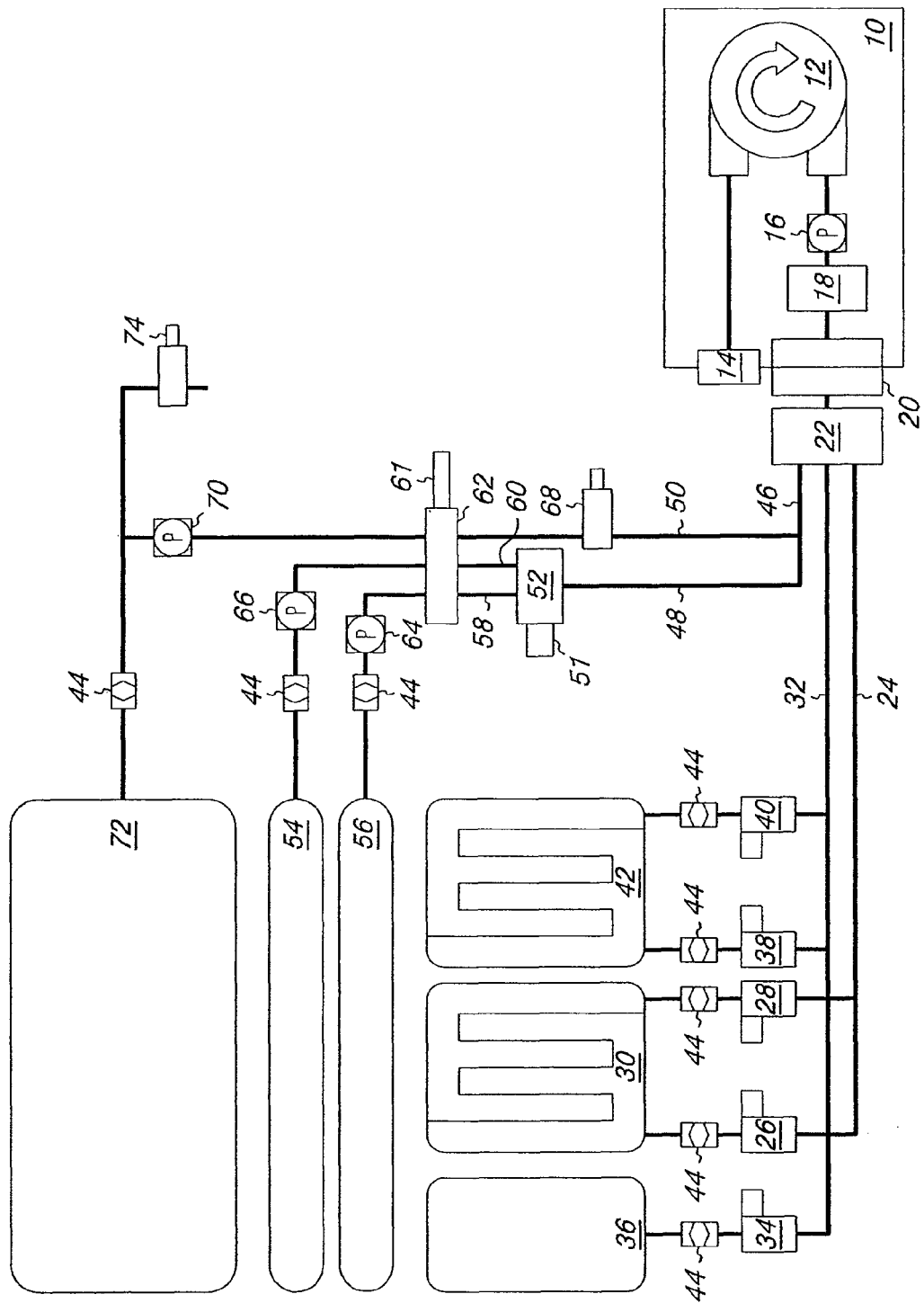
FIG. 1 is a schematic block diagram of the air flow components, conduits and connectors associated with implementation of the present invention.

An overview of the system of the present invention may be discussed by reference to the schematic drawing shown in FIG. 1. In this overview of the system, the mattress components are shown in relation to and interconnected with the various control components of the system. In various embodiments, blower box 10 can be comprised of a blower fan 12 that incorporates a dust filter 14 on its intake and an output that incorporates a pressure transducer 16 and passes through a heater unit 18 before being passed into the conduits of the system. The output of the blower box 10 is established through hose connector 20 that incorporates a manifold of air connections as well as electrical connections (not shown) in the same connector unit (described in more detail below). In various embodiments, hose connector 20 can be single piece or multi-piece connector and can include a number of components, such as springs, latches, and the like. Hose connector 20 mates with and connects to distribution block 22, which distributes the air flow from blower box 10 through three separate conduits. A first conduit 24 is connected to two proportional control valves 26 and 28 that are associated with the body cushion 30. A second conduit 32 is connected to proportional control valve 34 associated with head cushion 36, as well as proportional control valves 38 and 40 associated with foot cushion 42. Each of the proportional control valves mentioned is connected to its respective cushion by means of quick release connector 44.

Head cushion 36 is a single chamber unit (e.g., a single inflatable chamber) as is described in more detail below. The single chamber is connected by way of a quick release connector 44 to proportional control valve 34. Body cushion 30 is a multi-chamber unit (e.g., dual inflatable chambers) having interleaved chambers for alternating the pressurized air chamber for therapeutic purposes. Each of the two separate chambers is connected by way of a quick release connector 44 to the respective proportional control valves 26 and 28. Foot cushion 42 is a multi-chamber unit (e.g., dual inflatable chambers) structured much the same as body cushion 30, and incorporates two interleaved chambers that are individually connected by way of quick release connectors 44 to their respective proportional control valves 38 and 40. The specific construction of each of the cushion components of the system of the present invention is described in more detail below.

The control of the air pressure within head cushion 36, body cushion 30, and foot cushion 42 is described in greater detail herein below and forms part of the basic structure and functionality of the present invention. In general, however, these three cushion components are maintained in an inflated condition by the electronic control of proportional control valves and/or blower speed control under the operation of microprocessors or microcontrollers which include computer executable instructions, e.g., program instructions and/or algorithms that include therapeutic air inflation pressures and regimens, in addition to being connected one to another by way of a digital signal network.

In various embodiments, a third air conduit can be provided. In embodiments having the third air conduit, such as the embodiment shown in FIG. 3, the air conduit leaves from distribution block 22 to carry the flow of air to the remaining bladders associated with the mattress system of the present invention. This air conduit 46 is split between two conduits 48 and 50. Conduit 48 passes to a stepper actuated directional control valve 52 that alternately inflates and deflates turning bladders 54 and 56. Directional control valve 52 is operated by means of stepper motor 51. Air is distributed from directional control valve 52 through two conduits 58 and 60, which pass through manual CPR release block 62 which is monitored by CPR switch 61. Each of conduits 58 and 60 incorporate pressure transducers 64 and 66 and quick release connectors 44 as they pass into their respective turning bladders 54 and 56. The inflation of turning bladders 54 and 56 is generally accomplished in alternating fashion and is controlled by the directional control valve 52 so as to inflate one turning bladder and deflate the second turning bladder in a manner that rotates the patient to one side or the other. The orientation of the turning bladders lengthwise along the mattress system, as described in more detail below, makes this turning process possible.

Referring again to FIG. 1, in various embodiments, air conduit 50, extending from distribution block 22 by way of air conduit 46, can pass through an activation solenoid 68 and thereafter pass through CPR release block 62. From release block 62 air conduit 50 continues through a pressure transducer 70 and through a quick release connector 44 before finally serving to inflate MRS (mattress replacement system) bladder 72. MRS bladder 72 is provided with a vent to atmosphere by way of solenoid 74. In various embodiments, a foam cushion or mattress can be implemented and can replace the MRS 72 and its associated components. In such embodiments, components such as air conduit 50 for example, can be removed.

Figure 2:
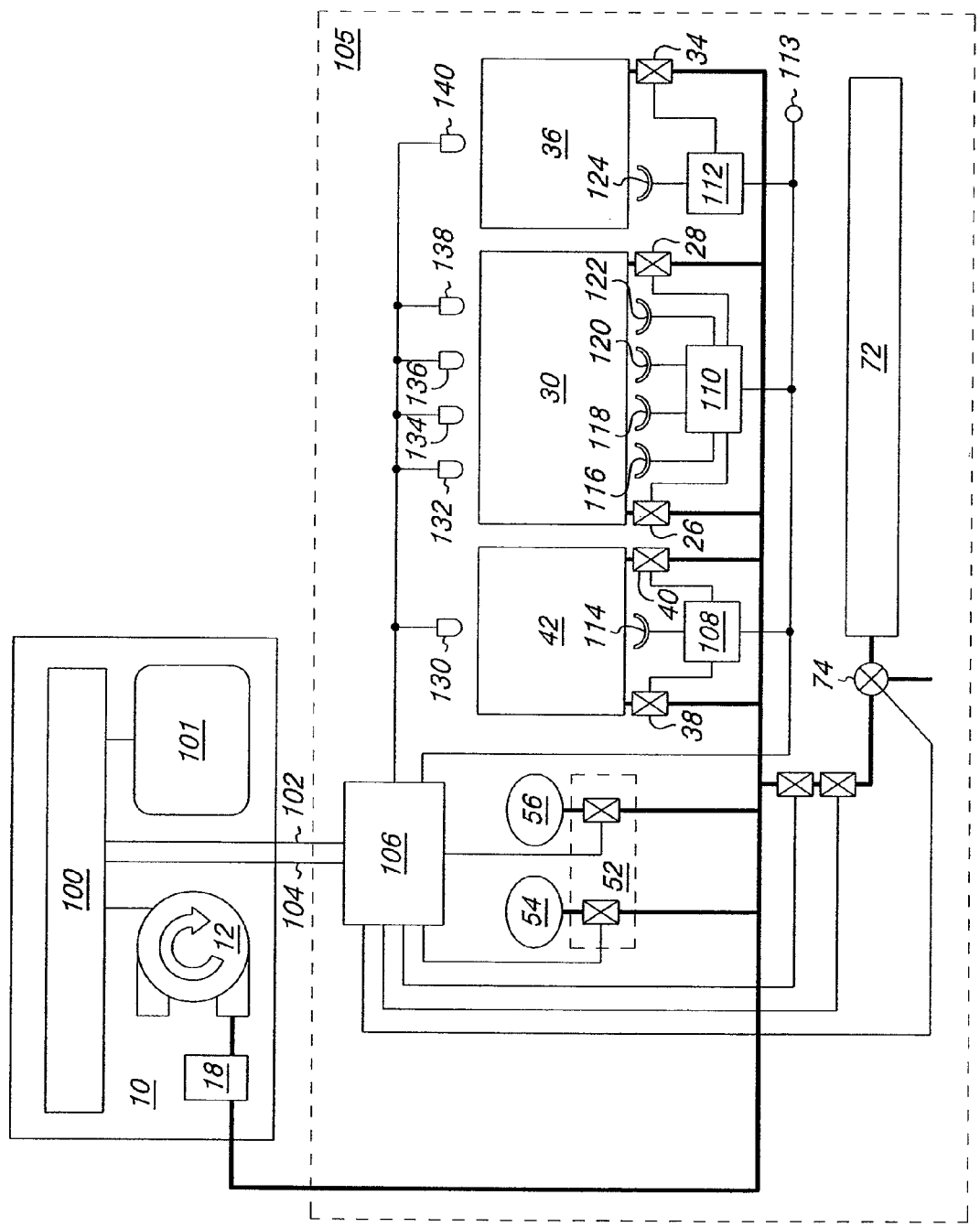
FIG. 2 is a schematic block diagram of both the primary air flow connections as well as the primary electronic signal connections for the overall system of the present invention.

The blower box 10 described above is generally incorporated into a user interface unit that mounts on the footboard of the bed on which the mattress system of the present invention is placed. In this user interface unit are contained some of the electronics associated with the programming and operation of the system, e.g., controller area network (CAN) nodes and other circuitry. Reference is now made to FIG. 2 for an overview of the control components associated with the system of the present invention and duplicates in part the overview pneumatic diagram described above with respect to FIG. 1. In FIG. 2, blower box 10 is again seen to include blower fan 12, which ultimately (albeit through a number of other manifold connectors not shown in this diagram) serves to provide the inflation air to left turning bladder 54, right turning bladder 56, foot cushion 42, body cushion 30, head cushion 36 and MRS bladder 72. The electrical connections shown in blower box 10 include the electric power necessary to run heater 18, which serves to warm the air after it passes out of the blower fan 12 as well as connections to a data I/O device 101, e.g., a user data interface (UDI), graphical user interface (GUI), among others, which in the preferred embodiment includes an LCD display having touchscreen functionality. Otherwise, the electrical/electronic connections from user interface 100 are shown as including a power connection 102 and a communications connection 104. As indicated above, these electrical/electronic connections are maintained through the same hose connector assembly 20 discussed above, and thereby form the electrical/electronic connection from the blower box to the mattress assembly.

The mattress assembly 105 itself incorporates a mattress controller 106 which receives both power and communication signals from user interface 100. The same power and communication lines are in turn relayed to stepper valve controllers associated with each of the three cushion components of the mattress system of the present invention. These controllers are established as "network nodes" and include stepper valve controller 108 (associated with the foot cushion 42), stepper valve controller 110 (associated with body cushion 30) and stepper valve controller 112 (associated with head cushion 36). Each of these stepper valve controllers is directly connected to both the infrared receivers associated with the cushion to which it is attached, as well as the control valves that direct the inflation of that cushion. Stepper valve controller 108, for example, receives signal from infrared receiver 114 and thereby controls valves 38 and 40 to maintain the appropriate inflation of foot cushion 42. Likewise, stepper valve controller 110 is associated with infrared receivers 116, 118, 120, and 122 as well as control valves 26 and 28, each associated with body cushion 30. Finally, stepper valve controller 112 is associated with infrared receiver 124 and control valve 34, which are each associated with head cushion 36. The networked structure of this chain of controllers makes it possible to add additional controllers at connector 113, which can be positioned at various locations including the stepper valve controllers 108, 110, and 112, as may be required by alternative cushion structures and functionality.

Referring further to FIG. 2, left turning bladder 54 and right turning bladder 56 are each controlled from the mattress controller 106 by means of the programmed operation of directional control valve 52 shown in split configuration in FIG. 2. Likewise, the inflation of MRS bladder 72 is controlled by way of mattress controller 106 by means of the programmed operation of MRS clamp solenoid 68 and MRS vent solenoid 74. In the preferred embodiment, the inflation of the MRS bladder may be varied to help establish the firmness of the overall mattress system while the turning bladders may, of course, be varied to accomplish the turning function described above. As discussed above, in some embodiments, a foam type cushion or mattress can be implemented and thus, in such embodiments, the mattress controller would not be utilized to control the foam mattress.

Figure 3:
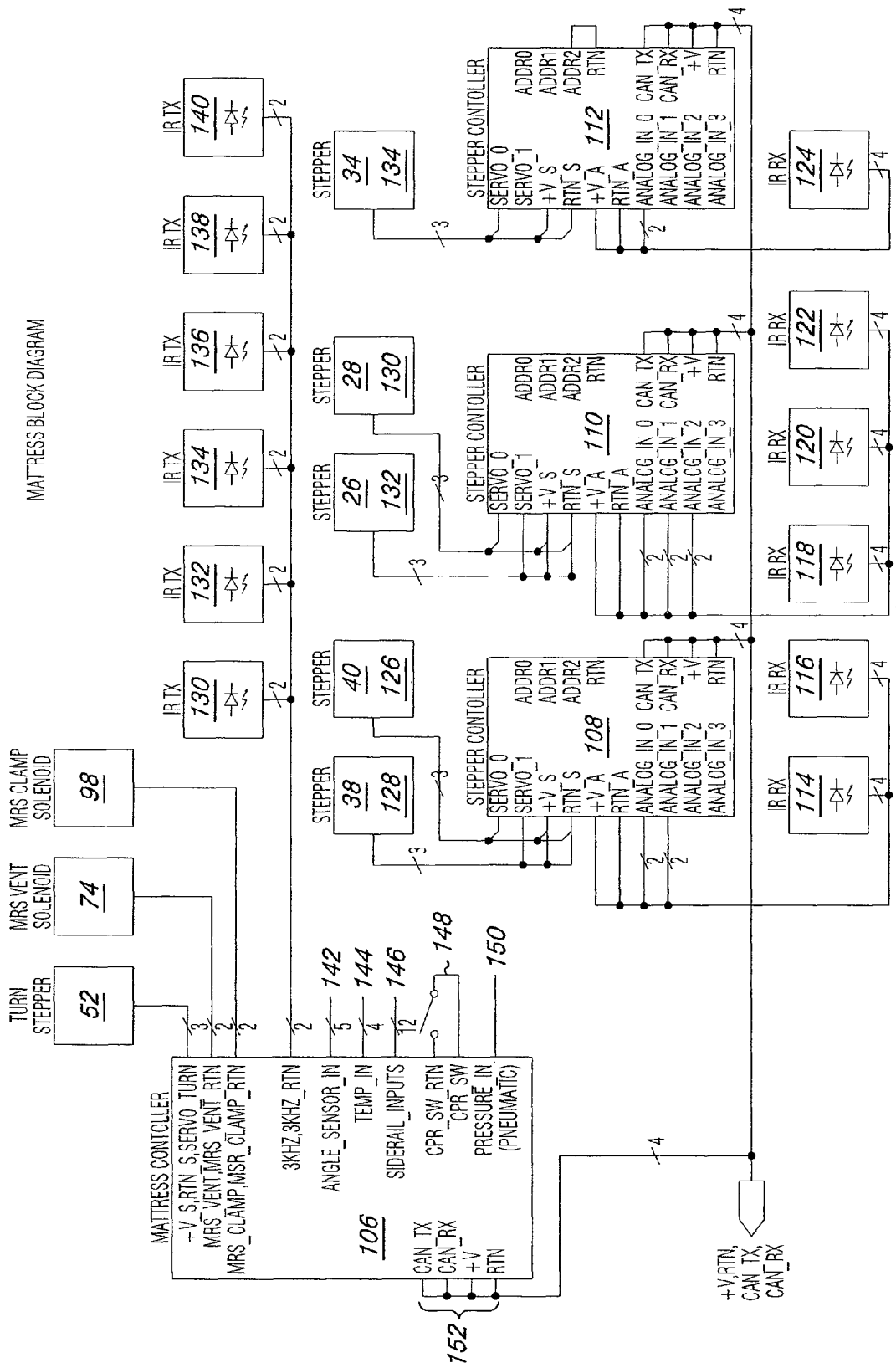
FIG. 3 is a detailed (system level) electronic schematic diagram of the mattress block diagram and sensor signal components of the present invention.

In various embodiments, the mattress controller can include a number of different configurations. For example, the mattress controller can include an MRS vent solenoid in embodiments that utilize the MRS bladder, as discussed herein. Reference is now made to FIG. 3 which shows in greater detail the controller network of the control interlayer for the mattress system of the present invention. Mattress controller 106 is shown having direct control connections to the stepper actuated directional control valve 52 associated with the turning bladders, as well as the MRS vent solenoid 74 and the MRS clamp solenoid 68. Likewise, mattress controller 106 serves to power (and illuminate) each of the infrared transmitters (six in the preferred embodiment) 130, 132, 134, 136, 138, and 140. These IR transmitters are IR light emitting diodes (LEDs) in the preferred embodiment and are operated in concert at the indicated 3 KHz signal frequency. Other frequencies are contemplated. Mattress controller 106 likewise receives input signal data from an angle sensor input 142, a temperature sensor input 144, and side rail position sensors input 146. A manual CPR switch 148 is associated with CPR release block 62 described above. A pressure-in connection 150 receives pneumatic air pressure measurements from pressure gauge 16 described above.

In various embodiments, mattress controller 106 forms a base network node for network connection 152 that includes the network transmission and receive signal lines as well as power voltage and return lines. This network connection 152 is distributed through to each of the stepper valve controllers mentioned above as network nodes 108, 110 and 112. These microcontrollers, again acting as nodes on the local network, individually receive input from the infrared receivers 114, 116, 118, 120, 122, and 124 associated with foot cushion 42, body cushion 30, and head cushion 36, respectively. In turn each of these controllers operates and controls the stepper motors connected to the proportional control valves described above. These stepper motors include stepper motor 126 associated with control valve 40 of foot cushion 42, stepper motor 128 associated with control valve 38 of foot cushion 42, stepper motor 130 associated with control valve 28 of body cushion 30, stepper motor 132 associated with control valve 26 of body cushion 30, and finally stepper motor 134 associated with control valve 34 of head cushion 36.

Each of stepper valve controllers 108, 110 and 112 are programmed controllers that are capable of independently maintaining the appropriate inflation of their respective cushions without relying on the network connection to the mattress controller 106 or to the connection back to the user interface unit 100. Each stepper valve controller acts as a network node in accordance with a CAN (controller area network) protocol as described in more detail below. This network structure serves to improve operation of the system as a whole and provides a highly efficient maintenance of the appropriate inflation of the mattress system components, even in response to movement by the patient that might otherwise result in "bottoming" through the mattress cushions. Each of the microcontrollers in the described preferred embodiment of the present invention may be satisfied by an H8/3687N type microcontroller IC or its equivalent. In various embodiments, the network structure can include a variety of CAN nodes, configurations, and protocols. In some embodiments, each of the stepper valve controllers and other controllers (e.g., mattress controller, and various valve controllers, among others) can be uniquely identified as nodes on the network by way of the indicated address jumpers. In other embodiments, nodes can be dynamically addressed. In some embodiments CAN nodes can be connected in a specific order and addressed in a specific order. For example, in one embodiment, CAN nodes can be connected in the following order: GUI (Network Supervisor), Blower Controller (BC), Mattress Controller (MC), Foot Valve Controller (FVC), Body Valve Controller (BVC), and Head Valve Controller (HVC). As one of ordinary skill in the art will appreciate, the various controllers can include similar controllers having the same or similar functions, and should not be limited to those described above. For example, the blower controller can include any controller that controls a rate of air flow from a blower, fan, or other source of pressurized fluid. In various embodiments, dynamic addressing can begin with a broadcast message sent on the network by the GUI node requesting all nodes to prepare for dynamic addressing. When a node receives this message, the node replies with a node identification message, which is an identification number given to each type of board. For example, in various embodiments, a BC node can have an identification number of 1, the MC node can have an identification number of 2, and a VC node can have an identification number of 3. The GUI node assigns a network address to each node that returns an identification number. In some embodiments, a sequential power-up sequence can also be implemented with the dynamic addressing process. For example, in some embodiments, when dynamic addressing begins, power is supplied to the GUI, BC, MC, and FVC nodes. After the BC, MC, and FVC nodes power up and get addressed, the FVC node relays power to the BVC node, which is the only valve controller (VC) node on the network without an address. The GUI will be able to differentiate it from the other VC nodes. Once the BVC node gets addressed it relays power to the HVC node and it is now the only VC node on the network without an address. Once the HVC node gets addressed the network is ready for normal use.

Figure 4:
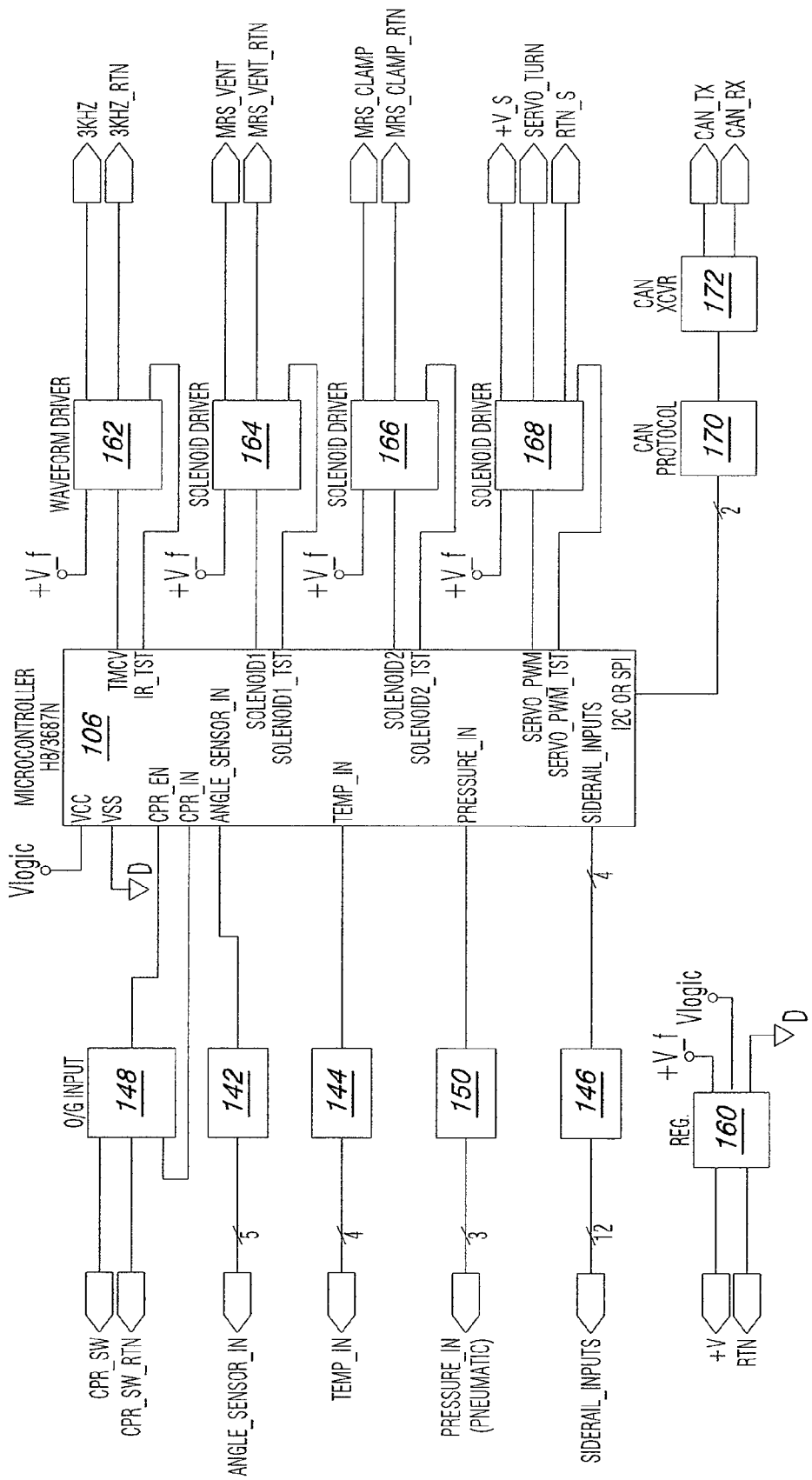
FIG. 4 is a detailed (controller level) electronic schematic block diagram of the mattress controller of the present invention and its associated drivers and inputs.

FIG. 4 provides further detail on mattress controller 106, showing the microcontroller and its connection to the various inputs and outputs associated with the controller. Included as O/G inputs are the CPR switch connections 148, the angle sensor connection 142, the temperature sensor connection 144, the pneumatic pressure sensor connection 150, and the side rail sensor inputs 146. The mattress controller circuitry shown in FIG. 4 also incorporates a voltage regulator 160 for powering the operation of the microcontroller and each of the ancillary components.

The outputs of the microcontroller 106 include the 3 KHz wave form driver 162 that powers and drives the infrared transmitters in concert as discussed above. The microcontroller also includes output signals to control solenoid drivers 164 and 166 that direct the MRS vent and clamp solenoids respectively. Finally, the microcontroller 106 operates the stepper motor driver 168 that controls the stepper actuated directional control valve which inflates and deflates the turning bladders. As mentioned above, microcontroller 106 is connected to and forms a node on the CAN and the mattress controller unit maintains the CAN network protocol circuitry 170, and the CAN transceiver circuitry 172.

Figure 5:
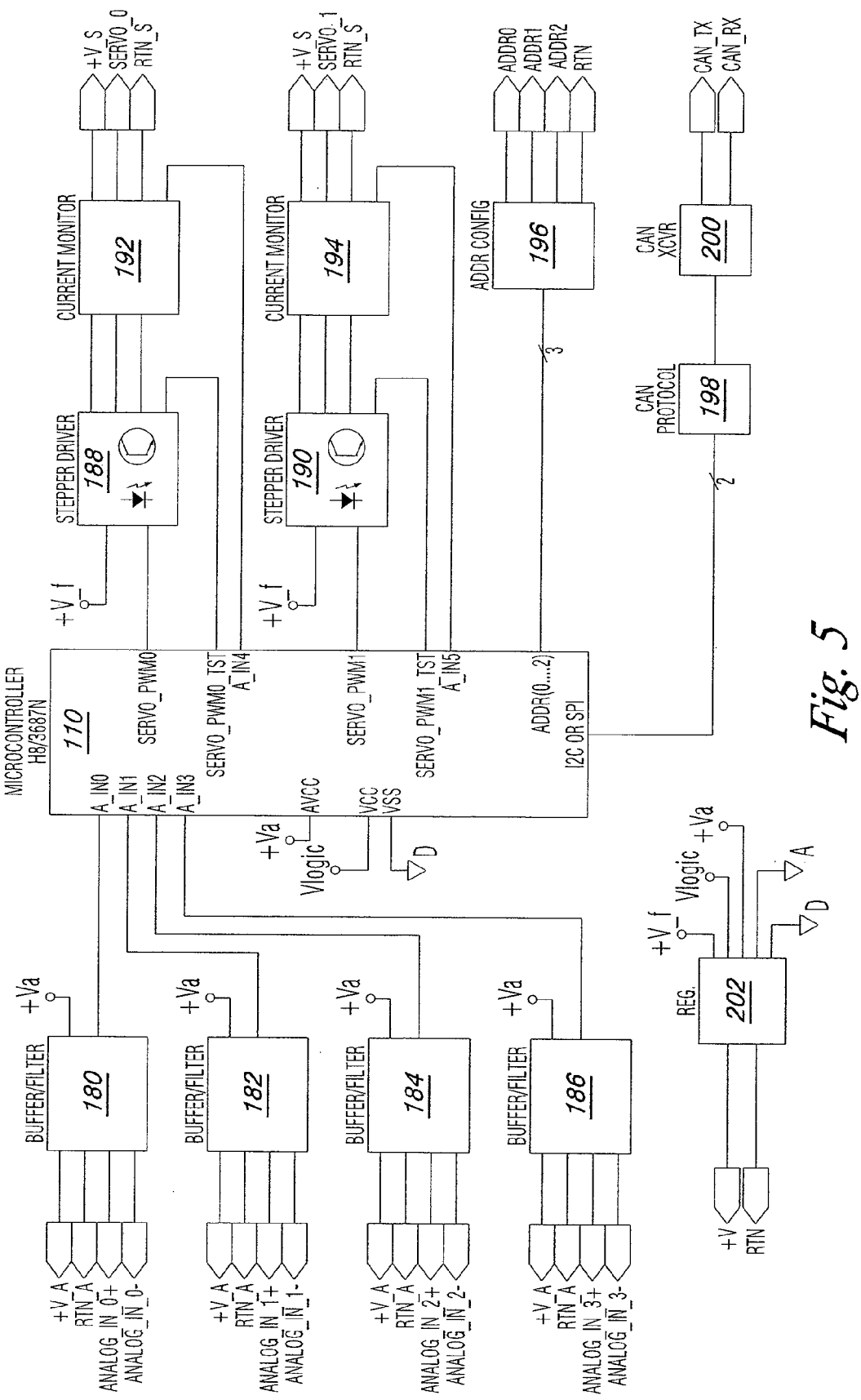
FIG. 5 is a detailed (controller level) electronic schematic block diagram of the stepper valve controller (cushion control) components of the present invention.

In various embodiments, the stepper controller can include a number of different configurations. For example, in some embodiments, the stepper controller can include one or more stepper driver circuits. In other embodiments, the stepper controller can include circuits for filtering, buffering, and gain. In some embodiments of the stepper controller, circuitry can be included or omitted which can be based on one or more desired functions to be elicited from the controller. In the embodiment illustrated in FIG. 5 a detailed diagram of the typical stepper valve controller is provided. This diagram describes a typical example of one of the three stepper valve controllers positioned in association with each of the three cushions in the preferred embodiment of the mattress system of the present invention. Stepper valve controller 110 associated with the body cushion is used in this example as it utilizes four input data signals associated with four IR sensors. Inputs to microcontroller 110 include buffered and filtered inputs from each of the infrared sensors as shown. Buffer/filter circuits 180, 182, 184 and 186 condition the analog signals from the individual IR sensor devices for appropriate monitoring by the microcontroller. The stepper valve controller likewise incorporates a voltage regulator 202 for powering the components in the controller circuitry.

Outputs from the microcontroller 110 (as in each stepper valve controller) include output signals for the stepper driver circuits 188 and 190 for the two proportional control valves under the control of the particular stepper valve controller. Operation of these drivers is accomplished through a current monitoring system 192 and 194 that allows the microcontroller direct feedback on the condition or state of the two proportional control valves. As indicated above, each microcontroller has an address configuration circuit 196 set to distinguish it from the other controller nodes on the network. Each microcontroller circuit likewise includes CAN protocol circuitry 198 and CAN transceiver circuitry 200 to maintain communications over the network.

The CAN (Controller Area Network) is a serial bus system that was originally developed for automotive applications in the early 1980's. The CAN protocol was internationally standardized in 1993 as ISO 11898-1 and comprises the data link layer of the seven layer ISO/OSI reference model. CAN, which is now available from a large number of semiconductor manufacturers in hardware form, provides two communication services: the sending of a message (data frame transmission) and the requesting of a message (remote transmission request, RTR). All other services such as error signaling, and automatic re-transmission of erroneous frames are user-transparent, which means the CAN circuitry will automatically perform these services without the need for specific programming.

The CAN controller is comparable to a printer or a typewriter and CAN uses, such as in the present application, still must define the language/grammar and the words/vocabulary to communicate. CAN does, however, provide a multi-master hierarchy, which allows the building of intelligent and redundant systems which is, as mentioned above, a feature of particular importance in the operation of the inflation maintenance objectives of the present invention. If one network node is defective, the network is still able to operate. CAN also provides broadcast communication wherein a sender of information may transmit to all devices on the bus simultaneously. Thus, programming through the user interface of the present invention may be distributed to each of the controller nodes on the CAN in a manner that may effect a regimen alteration throughout the system. All receiving devices read the message and then decide if it is relevant to them. This guarantees data integrity because all devices in the system use the same information. CAN also provides sophisticated error detection mechanisms and re-transmission of faulty messages.

Figure 6:
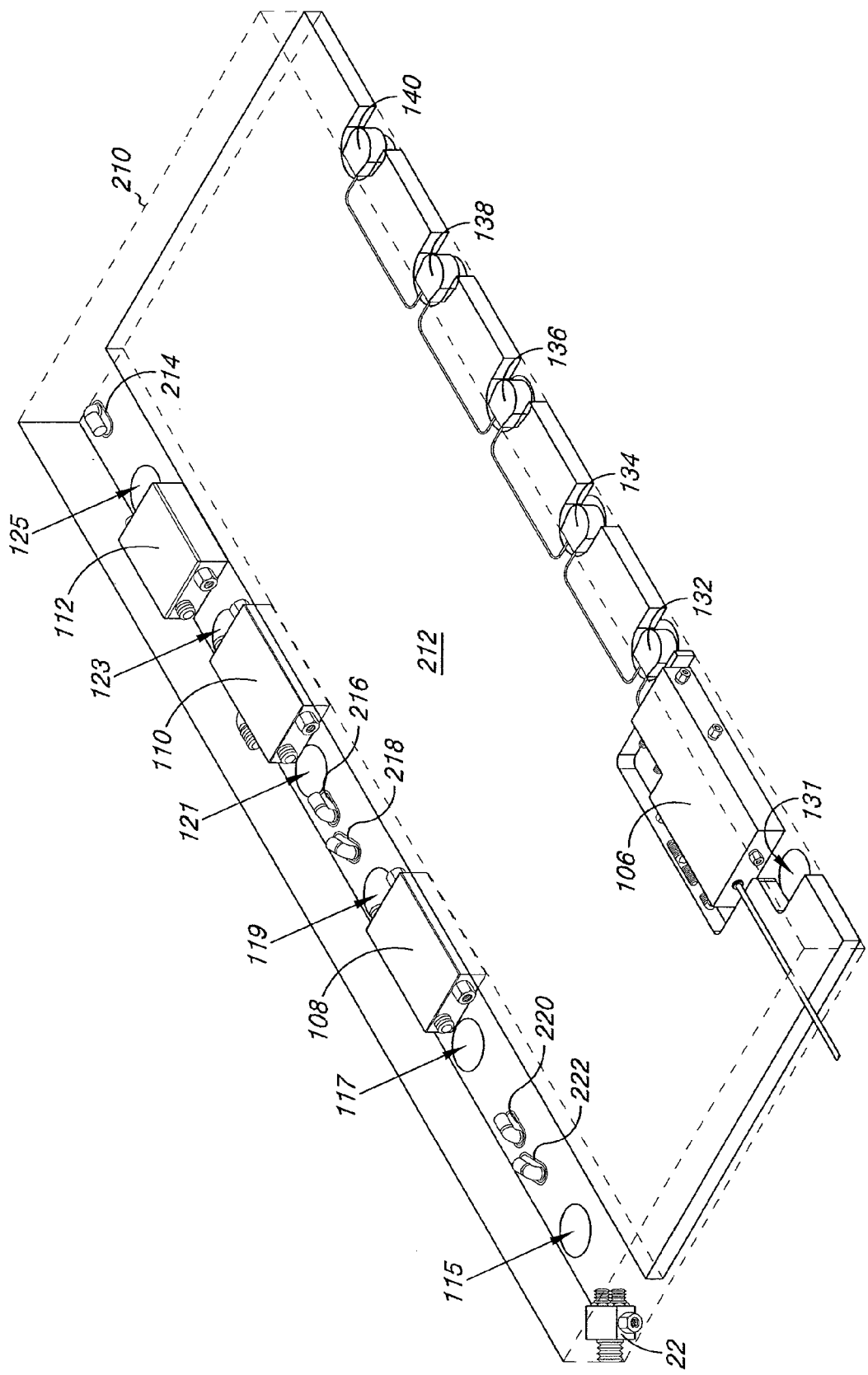
FIG. 6 is a perspective view of the underside of the controller interlayer of the mattress system of the present invention.
Figure 7:
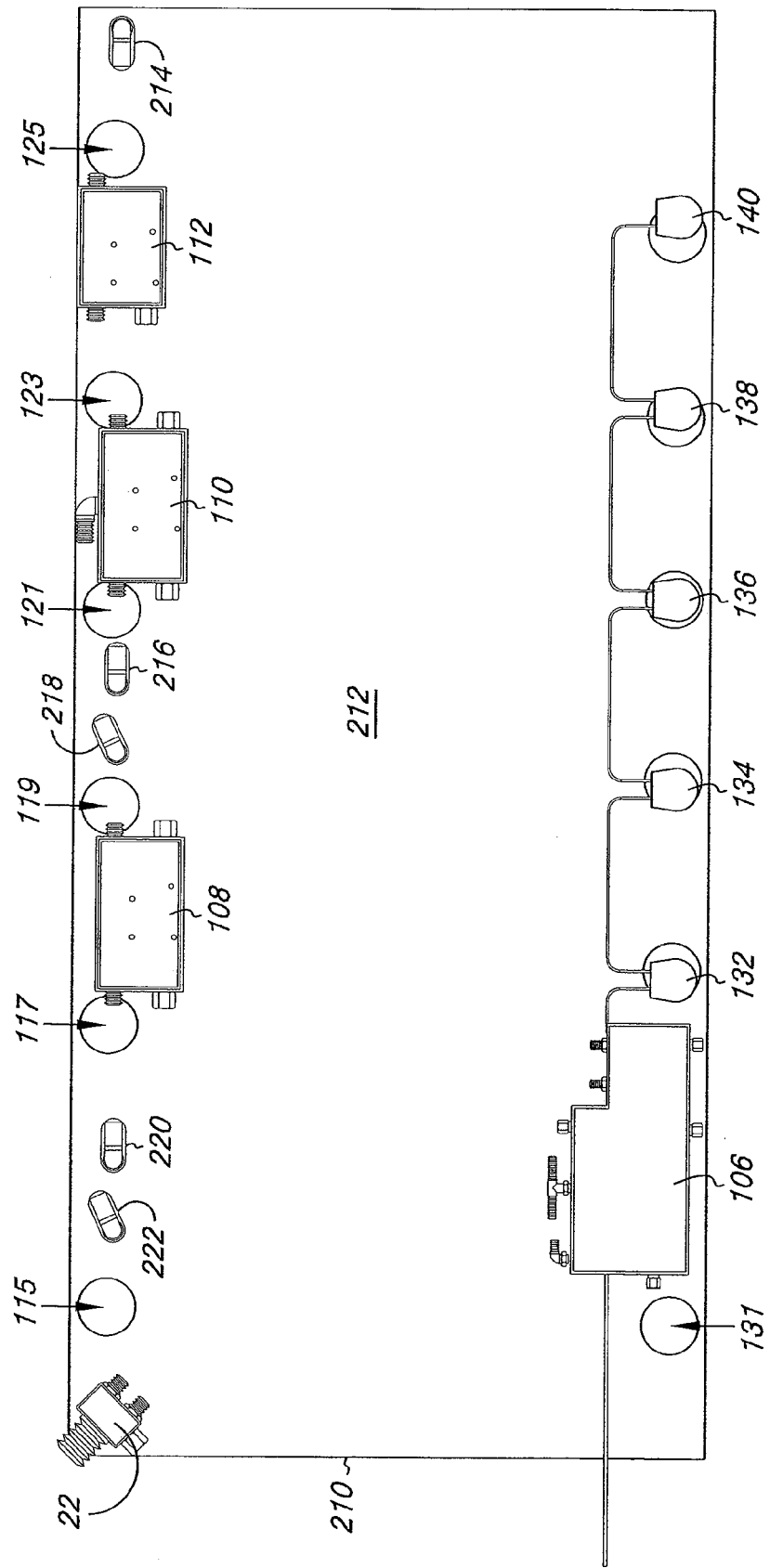
FIG. 7 is a plan view of the underside of the controller interlayer of the mattress system of the present invention.

Reference is now made to FIGS. 6 & 7 for a description of the physical placements of the various control components identified and discussed above. FIGS. 6 & 7 show, in perspective and plan views respectively, the underside of the control interlayer that is incorporated into the mattress system of the present invention. These views reflect the positions of the indicated components as they would be seen if the mattress system were flipped over and the MRS bladder and turning bladders were removed (this overall structure is described in more detail below with respect to FIG. 15). The controller interlayer is constructed primarily of flexible walled enclosure 210 surrounding a foam core 212 within which are positioned the various control components of the present invention. Mattress controller 106 is positioned as shown, as are stepper valve controllers 108, 110 and 112. The stepper valve controllers are positioned so as to be proximate to the cushion component for which they are specifically responsible. All but one of the IR transmitters are shown in place and connected together in concert. IR transmitters 132, 134, 136, 138 and 140 are shown in place in FIGS. 6 & 7. IR transmitter 130 has been removed to show the placement of IR transmitter window 131 positioned to receive placement of the transmitter on one side of controller 106.

On an opposite side of the control interlayer are the IR sensors, or more specifically shown in FIGS. 6 & 7, the IR sensor windows into the individual cushions, as described in more detail below. Sensor windows 115, 117, 119, 121, 123 and 125 are shown in FIGS. 6 & 7 positioned in association with their respective foot, body and head cushion components. Also associated with the appropriate cushion components are air flow inlet connectors 214 (associated with the head cushion), connectors 216 and 218 (associated with the body cushion) and connectors 220 and 222 (associated with the foot cushion). Manifold 22 is shown positioned to receive the single large air flow hose (not shown) to separate and distribute the air flow to three smaller conduits for subsequent distribution to the cushions and mattress components. In FIGS. 6 & 7 all air flow conduits have been removed for clarity. From manifold 22 two air flow conduits would connect with stepper valve controllers 108, 110 and 112 to provide the necessary air flow into the mattress cushions. A third air flow conduit connects from manifold 22 to mattress controller 106 where the necessary air flow is provided to the turning bladders and the primary MRS bladder as described above.

Also removed for clarity in FIGS. 6 & 7 are most of the electrical/electronic connections between the various control components. The exception to this is the 2-wire connection linking each of the IR transmitters together along one edge of the interlayer. In normal operation, a sixth IR transmitter 130 would be positioned over window 131 and would likewise be linked to the 2-wire circuit that is shown. Additional electrical/electronic connections between the components would be present as described above with respect to FIG. 2. In addition, the hardwired network connections between the controller enclosures, as shown and described in association with FIGS. 3-5, would also be present.

Figure 8:
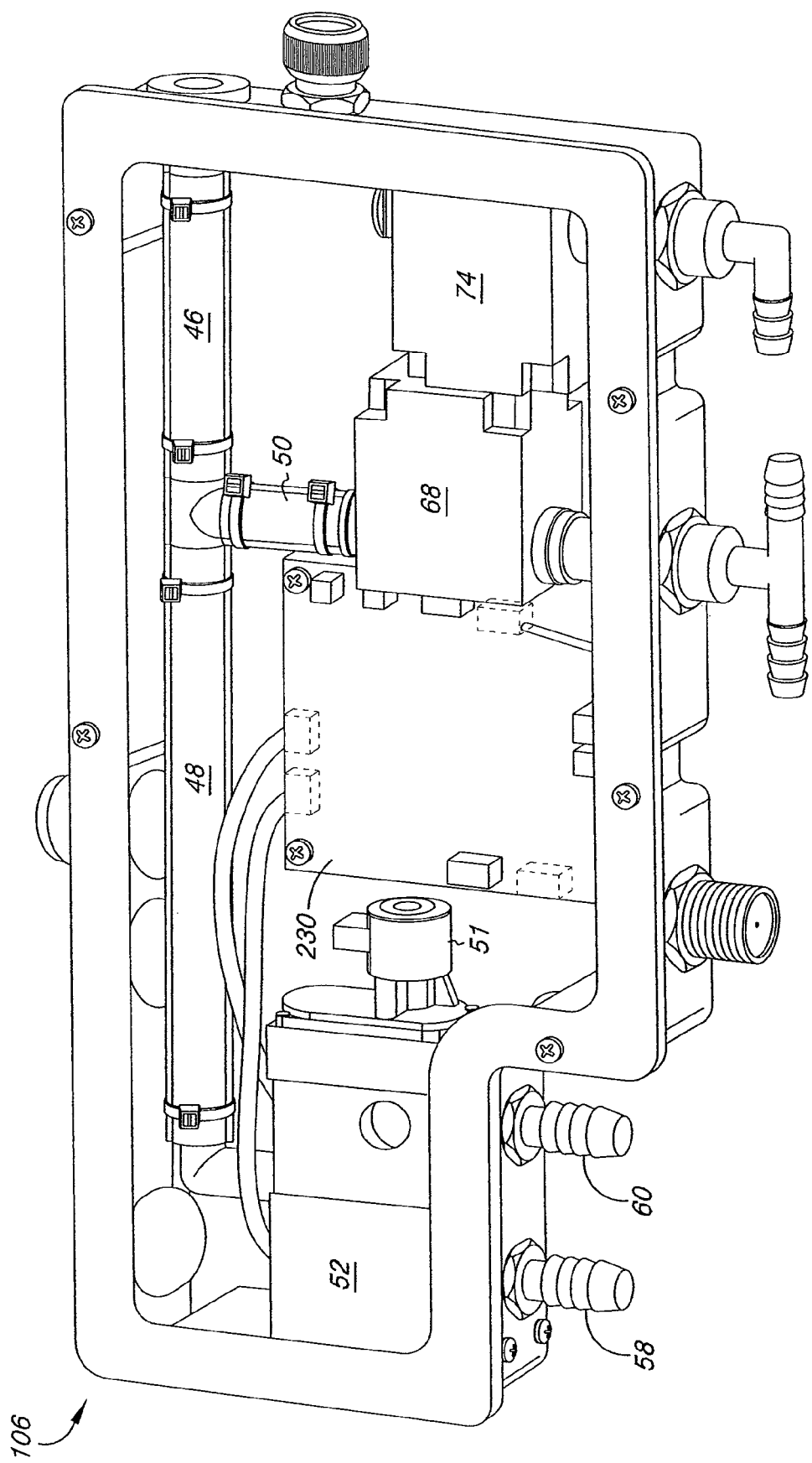
FIG. 8 is a detailed perspective view of the mattress controller enclosure of the system of the present invention.

Reference is now made to FIG. 8 for a brief description of the mattress controller 106 and its enclosure. Various electronics and electromechanical controls are included within the mattress enclosure controller. The air flow source is by way of conduit 46 which feeds conduit 48 and conduit 50. Conduit 48 provides air flow to stepper actuated directional control valve 52 which is driven by stepper motor 51. This provides the necessary air flow to the turning bladders by way of conduit connections 58 and 60.

Conduit 50 provides air flow to solenoid valve 68 which in turn directs air flow out of the enclosure to the MRS bladder and to a vent through solenoid valve 74. Each of the solenoid valves 68 and 74, as well as directional control valve 52, are electrically connected to PC board 230 on which the controller circuitry described above (for the mattress controller) is provided. The micro-controller IC is likewise positioned on PC board 230 and forms the core of the controller as a whole. The electrical/electronic connections discussed above are generally not shown in FIG. 8 for clarity but would enter the enclosure through the ports, some of which can be water tight, shown on the sides of the enclosure. A lid (not shown) would complete the walled enclosure to generally seal it against fluids.

Figure 9:
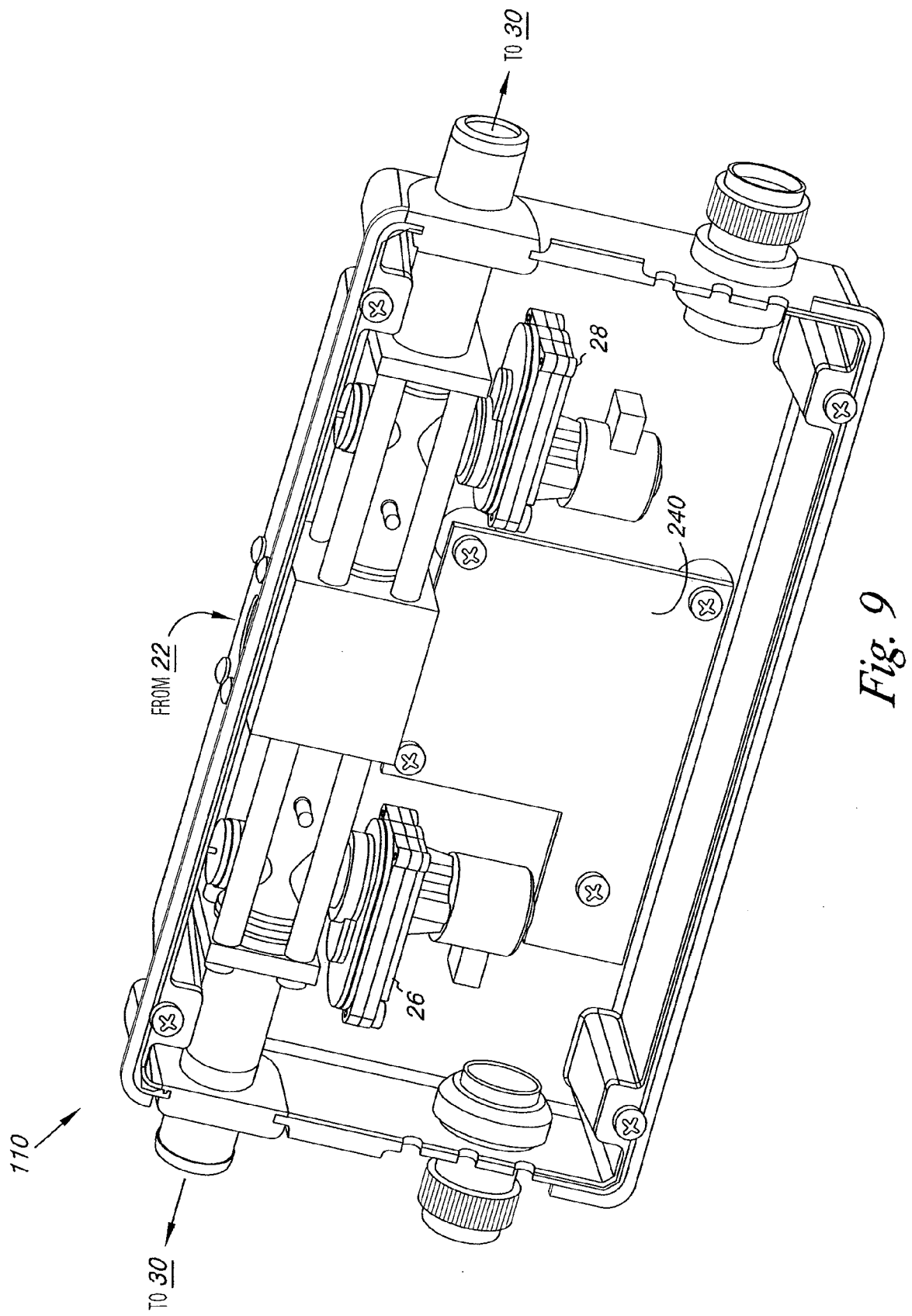
FIG. 9 is a detailed perspective view of a stepper valve (cushion) controller enclosure of the system of the present invention.
Figure 10A:
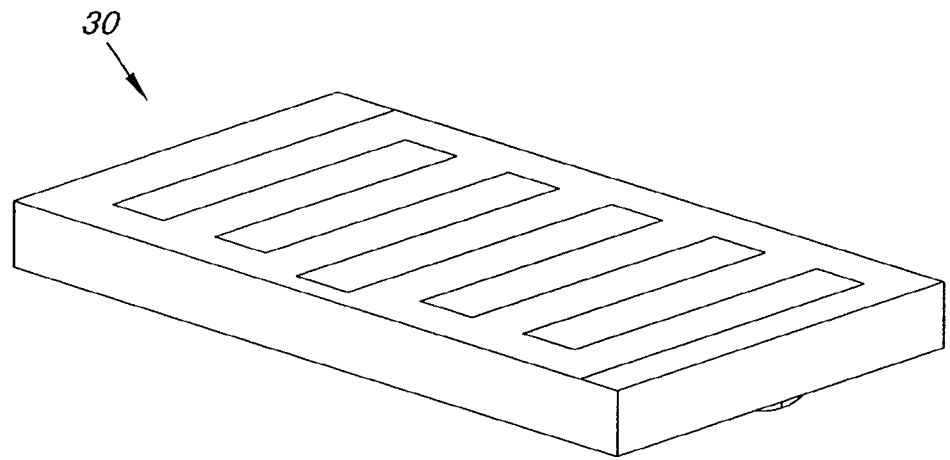
FIGS. 10A & 10B are perspective views (top and bottom) of the body cushion mattress component of the system of the present invention.
Figure 10B:
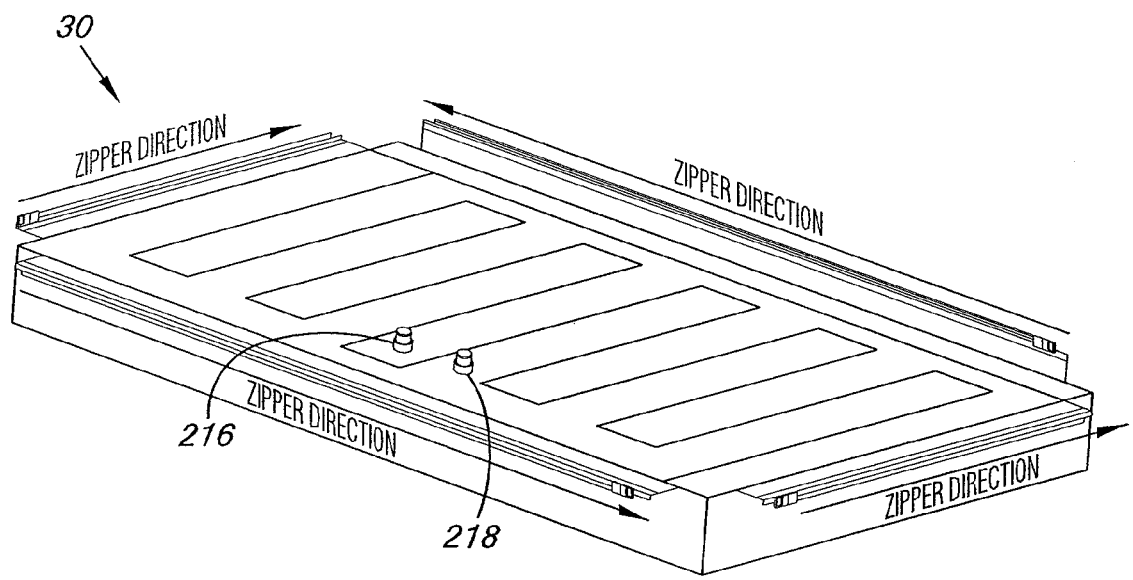

Reference is now made to FIG. 9 for a brief description of a representative example of the stepper valve controllers that operate in conjunction with the mattress controller and provide the regulated air flow to the mattress cushions as described above. In FIG. 9, stepper valve controller 110, which services the requirements of the body cushion 30 of the system, is shown as an example. It is understood that the remaining two stepper valve controllers would be either identical in structure or would comprise one-half of the operational components of the example shown. In this view, stepper motor driven proportional control valves 26 and 28 are shown. The source of air flow to the unit is shown on one side of the enclosure at "From 22", indicating the source as coming from the manifold 22. Outflow of air from the control valves is directed to body cushion 30 by way of the indicated connectors on the opposite sides of the enclosure. Each of the control valves 26 and 28 are electrically connected to PC board 240 on which the controller circuitry is provided. Here again, the electrical/electronic connections (wires) both within the enclosure and into and out of the enclosure are omitted for clarity. Control of the valve operation includes monitoring the rate of valve openings and closings in an effort to reduce overall valve noise associated with the operation of the system. In addition, control of the stepper motors involves monitoring of current as a means of error checking the control signal. The PC boards in the three stepper valve controller enclosures are essentially the same and are distinguished on the network as they are dynamically addressed during installation. Because of the distributed processing structure of the network of the system, it is possible to power-up and activate individual nodes/controllers on the system in progressive fashion. This greatly facilitates both initial implementation and subsequent maintenance of the system. A diagnostic mode of operation also facilitates these aspects of the distributed network.

Reference is now made to FIGS. 10-13 for a description of the construction and configuration of the cushions associated with the mattress replacement system of the present invention. FIGS. 10A and 10B show the general construction of the body cushion 30 of the system of the present invention. As shown in FIG. 1 above, body cushion is generally constructed with two interleaved chambers so as to provide alternating pulsation air flow into the cushion as a known therapy for bedridden patients. These chambers are constructed of generally box shaped channels that run parallel across the cushion. The topside view of body cushion 30 is shown in FIG. 10A and by way of the fabric seams shown, indicates the configuration of the interleaved channels. Air flow inlet connectors 216 and 218 are shown in FIG. 10B (a view of the underside of the cushion) where they would align with and connect to their corresponding connections on the control interlayer discussed above.

The construction of body cushion 30 is of any of a number of different high and/or low air loss fabrics that provide the airflow "outlet" for the air inflation system, as is generally known in the art. The cushion is generally constructed by sewing techniques "inside out" and is then turned "right side out" though an initially open section of the seam (shown in FIG. 10A). The mattress cushions of the present invention may be sewn as indicated above or may be RF (radio frequency) welded as is known in the art. The finished cushion is maintained in its position in the mattress replacement system by way of the indicated zippers (or similar attachment means) to corresponding zipper components (or similar attachment means) on the mattress replacement system enclosure material.

Figure 11A:
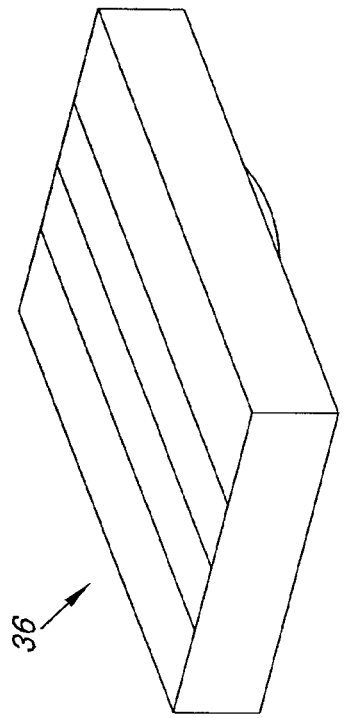
FIGS. 11A & 11B are perspective views (top and bottom) of the foot cushion mattress component of the system of the present invention.
Figure 11B:
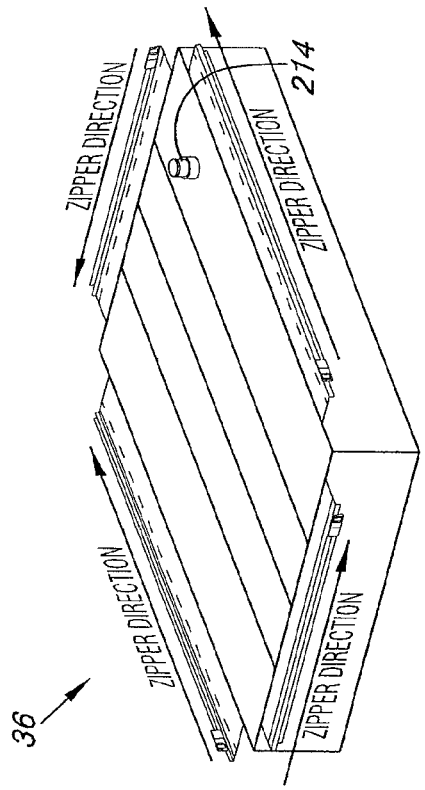

FIGS. 11A and 11B disclose the construction of foot cushion 42 which, like body cushion 30, is constructed of two interleaved chambers. Air flow connectors 220 and 222 are shown in FIG. 11B (the underside view of the cushion). The construction techniques for foot cushion 42 are the same as those described above for body cushion 30.

Figure 12A:
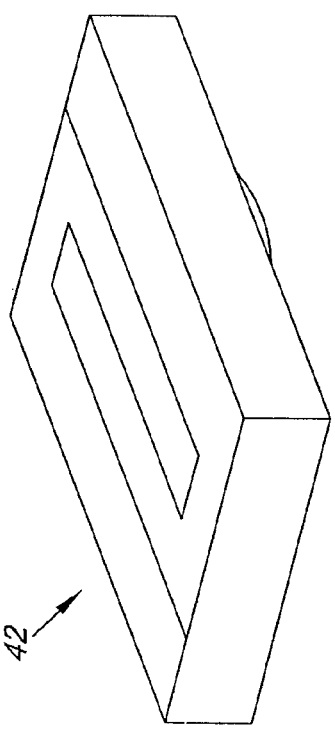
FIGS. 12A & 12B are perspective views (top and bottom) of the head cushion mattress component of the system of the present invention.
Figure 12B:
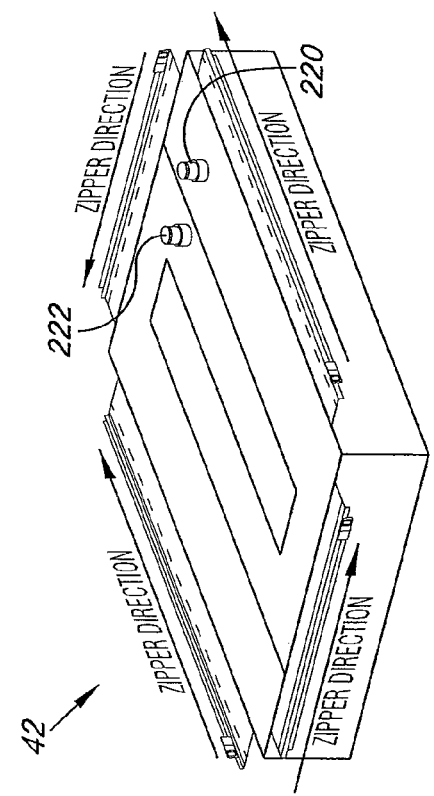

FIGS. 12A and 12B disclose the construction of head cushion 36 which differs from the construction of body cushion 30 and foot cushion 42. Head cushion 36 is not designed to be subjected to an alternating chamber pressurization therapy and is therefore constructed of a single chamber with a single air flow inlet connector 214 shown in FIG. 12B (the underside view of the cushion). Parallel "channels" are still sewn or otherwise integrated into the cushion as shown in FIG. 12A for the purpose of maintaining the flat configuration of the cushion, but interior air flow between these "channels" is provided for, resulting in an integrated interior chamber.

Figure 13:
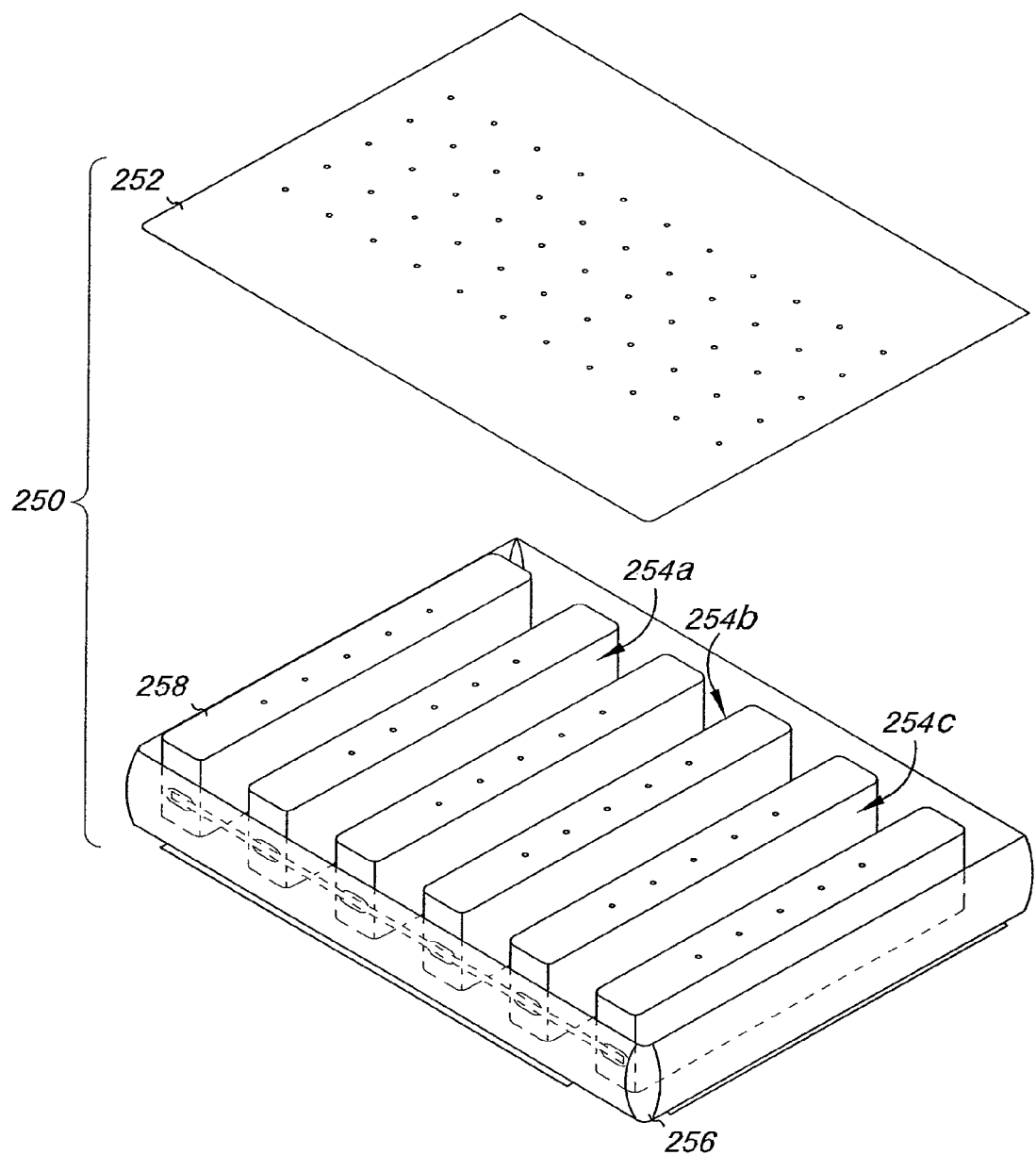
FIG. 13 is an exploded perspective view of an alternative embodiment of the body cushion mattress component of the system of the present invention showing placement of IR reflective surfaces.

Reference is now made to FIG. 13 for a brief description of one manner of interior cushion construction that integrates IR reflective surfaces to facilitate the measurement of the IR illumination with the cushion by the IR sensors. In this example of cushion construction, cushion 250 is made up of fabric box envelop 256 and top surface 252 shown separated in this exploded view for clarity. The important distinguishing feature in this construction is the placement of IR reflective surfaces 254a, 254b and 254c (a variety of which are known in the art) on specific interior sides of the box shaped channels formed within the cushion. In this manner, discrete portions of the cushion become the focus of the IR illumination (thereby allowing the system to better identify the portion of the cushion that may require greater inflation) and help to prevent "cross-talk" between the IR illuminated sections of the cushion. These features, when combined with the manner of timed polling of the IR sensors discussed in more detail below, serve to provide a more accurate indication of the portion of the cushion that may require modified inflation pressures. Although the chamber construction of the cushion 250 shown in FIG. 13 is somewhat different than the chamber construction shown in FIGS. 10-12 the principle of IR reflective surfaces strategically placed on the interior walls of the box shaped channels is easily applicable.

Figure 14:
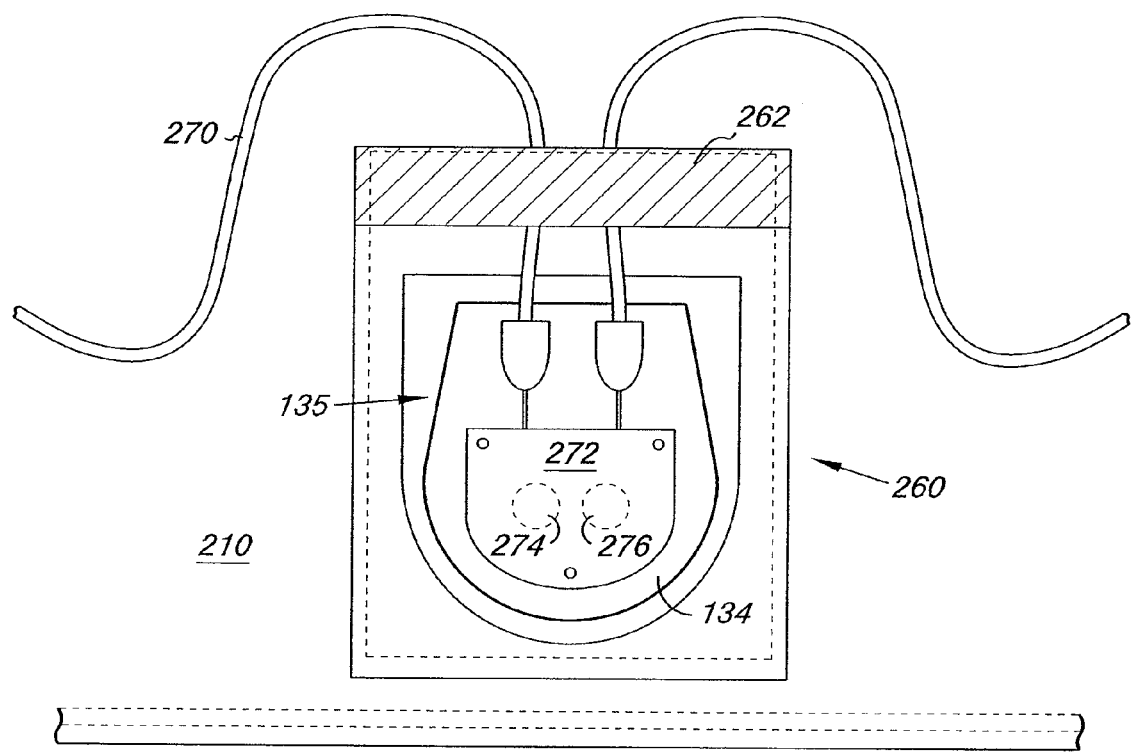
FIG. 14 is a detailed plan view of an IR receiver/transmitter (i.e., sensor/emitter) component of the system of the present invention.

FIG. 14 is a detailed plan view of a representative IR transmitter/sensor device of the system of the present invention. An objective in the design of the IR device is a single structure that may be configured to function either as the IR transmitter or the IR sensor. Used as an example in FIG. 14 is IR transmitter 134 shown positioned over window 135 in control interlayer envelope material 210. Transmitter 134 is positioned in a pocket 260 constructed of pliable polymer sheet material (such as a polyurethane material) capable of being sewn or welded to the material of the interlayer envelope. The pocket 260 is sized so as to both retain and position the IR transmitter 134. Closure material 262 is positioned across the opening of pocket 260 to provide retention of the device within the pocket. Closure 262 is not necessarily water tight as the construction of the IR transmitter itself is, in the preferred embodiment, a generally water tight enclosure. Hook and loop type material would be one appropriate structure for closure means 262.

IR transmitter/sensor 134 may include an injection molded rigid plastic enclosure having at least one side transparent to IR illumination that is directed into the associated cushion chamber. Within the rigid plastic enclosure is positioned PC board 272 on which are positioned IR LED 274 and/or IR sensor 276. A number of IR light sources (typically solid state LED devices) and IR sensors are commercially available that are suitable for use in conjunction with the system of the present invention. The circuitry associated with the IR sensors utilized in the preferred embodiment is configured to operate the sensors in the linear region of their output (typically the saturated region) and incorporates an auto gain adjustment to place the sensor into the linear region. In this manner, a more accurate and direct correlation between illumination levels and sensor output is achieved. This approach is particularly important for smaller displacements of the mattress cushion chamber being monitored (smaller changes in the illumination level) that under previous approaches might have been missed.

In addition, optical filters are utilized in the preferred embodiment of the present invention to narrow the IR frequency band received and monitored. This bandwidth narrowing allows for an optimal auto gain adjustment to put the sensors into the linear region of their output as described above.

Although the circuitry of the system for driving the IR transmitters described above drives the devices in concert, an alternative approach would drive the transmitters and poll the corresponding sensors in banks so as to further avoid the effects of "cross talk" between chambers. Avoiding the simultaneous polling of sensor/transmitter pairs that are directed to adjacent chambers at the same time would serve to diminish or eliminate such cross talk (light from one transmitter being picked up by a sensor from a different transmitter/sensor pair).

Figure 15:
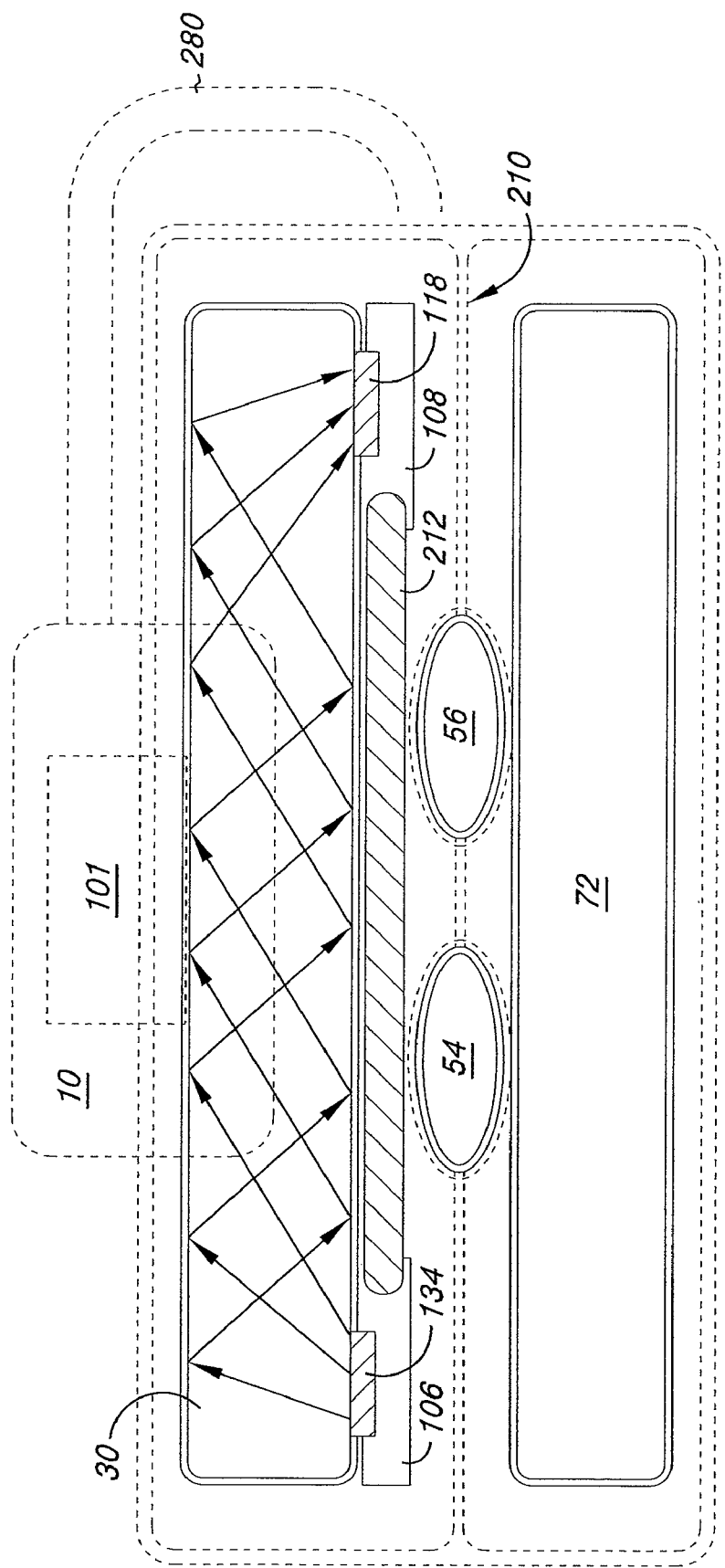
FIG. 15 is a schematic cross sectional view of the mattress, sensor and control components of the system of the present invention.

Reference is now made to FIG. 15 for a description of the manner in which the system of the present invention utilizes a measurement of IR illumination within an inflated chamber to determine when a decrease in chamber height warrants an increase in inflation pressure to that chamber to re-elevate the chamber. FIG. 15 also provides a description of the layered arrangement of the bladder components of the system of the present invention. The mattress replacement system is intended to be placed on existing hospital bed structures and the like although the principles of operation may readily translate into original equipment manufacturing designs. In the replacement environment the system comprises MRS bladder 72 surrounded in part by system envelope 210. Turning bladders 54 and 56 are likewise enclosed in envelope 210 and are, in the preferred embodiment, further positioned and retained within sub-envelopes integrated into envelope 210. Various compartments and sub-envelopes may be created within envelope 210 as necessary to position and retain the various bladders, control components, cables and air flow conduits. These compartments may be sewn or welded together or they may be constructed with sections of material that removably attach one to another with zippers or hook and loop attachment surfaces. Straps sewn into the envelope and secured with buckles and ties may also be utilized to position and retain the various components of the system in place.

The control interlayer of the system is further shown in FIG. 15 as a cross section generally from side to side on the bed through the center of the mattress system. In this location, body cushion 30 is shown with IR transmitter 134 positioned on one side of the cushion and IR sensor 118 positioned on an opposite side. Mattress controller 106 (which retains the circuitry to drive the IR transmitters) is shown, as is stepper valve controller 108 (which is responsible for the inflation of body cushion 30). Foam interlayer core material 212 is also seen in cross section in this view. Shown in dashed line form are the exterior components of the system, namely blower box 10 with display 101 and primary air flow conduit 280, as they would be positioned on the bed in association with the replacement mattress system.

Operation of the IR sensor system is structured to be a measurement of illumination level within a chamber as opposed to simply the interruption of a line of sight beam of IR light. Thus the orientation of the IR transmitter and the IR sensor is not one towards the other but rather into the chamber as a whole. Light paths shown in FIG. 15 within cushion 30 (within one or more cross-bed box shaped channel of cushion 30) represent the direction, dispersion and internal reflection of the IR light within the chamber and its eventual reception at the IR sensor. From this it can be seen how even slight modifications to the upper planar surface of the cushion will result in a decrease in the level of illumination received at the sensor. Significant changes in the planar surface, such as might occur if an elbow or other narrowly focused pressure were directed onto the outside surface of the cushion, would result in a more significant change in the overall level of illumination received at the sensor. In this manner, a more accurate determination of the degree of surface displacement, and of the danger of "bottoming out" can be achieved. The controllers described above and their direct connection to a bank of IR sensors as well as their direct connection to air inflation valves are therefore configured to provide a more immediate and appropriate response to the need for increased (or decreased) inflation pressures in any specific portion of the mattress system.

Figure 16:
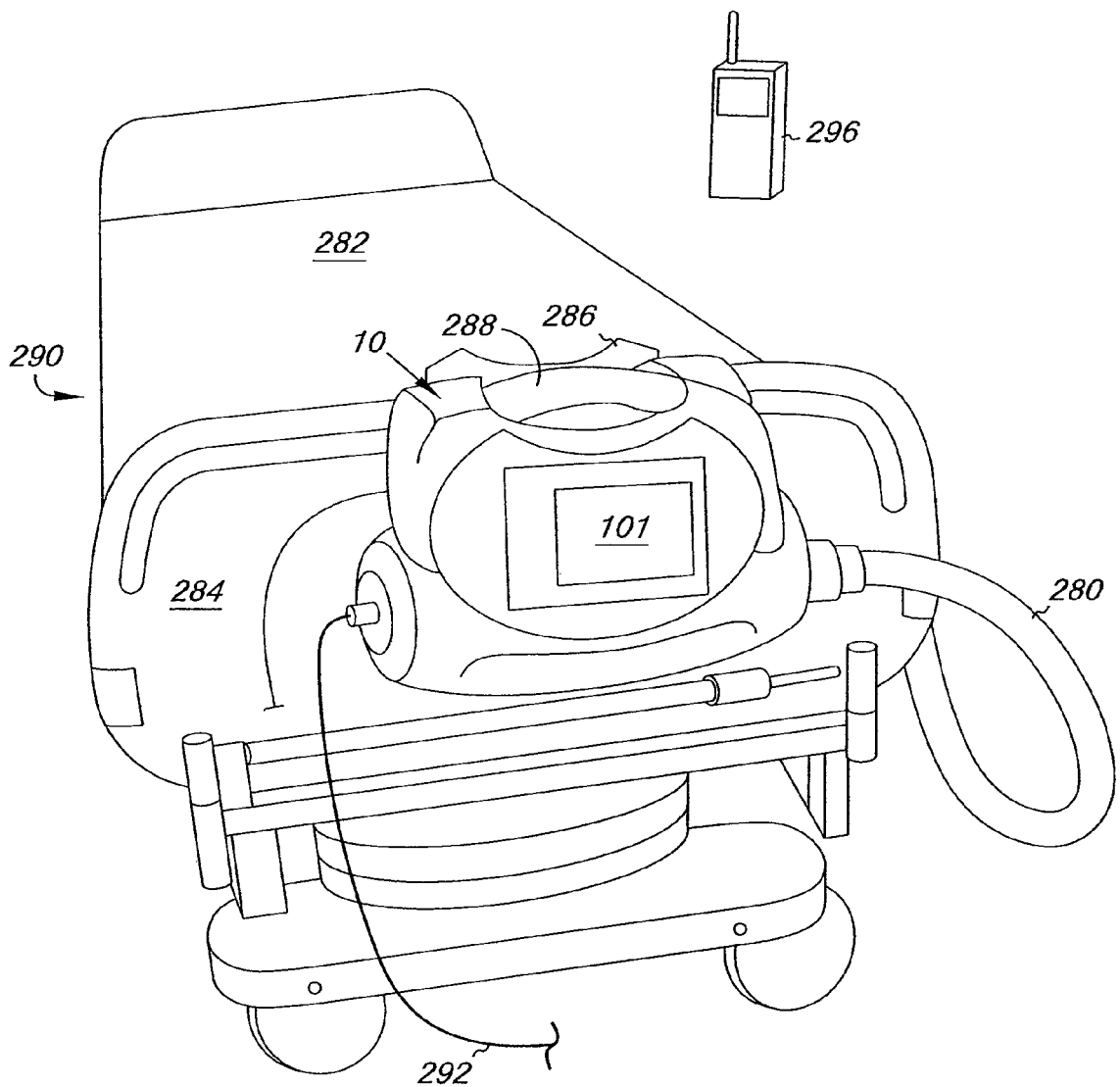
FIG. 16 is a perspective view of the installation of the system of the present invention on a typical hospital bed frame.

Reference is finally made to FIG. 16 for a brief description of the manner in which the system of the present invention may be positioned on a standard hospital bed or the like. In this view, bed 290 is configured with footboard panel 284 onto which is placed and positioned the blower box enclosure 10 of the present invention. Replacement mattress system 282 is shown positioned on bed 290 much in the same manner that a standard mattress might be placed. Clamp 286 is a rigid panel connected to blower box 10 in an adjustable fashion that allows the blower box to be retained and secured to the footboard panel 284. Blower box enclosure 10 incorporates an ergonomic handle 288 to facilitate its placement onto, and removal from, the bed. Primary air flow conduit connects the blower box 10 to manifold 22 (not seen in this view) associated with the interlayer of the mattress system 282. As mentioned above, the requisite electrical/electronic cables and connections between the blower box and the control interlayer are incorporated into the structure of the primary air flow conduit so as to eliminate the need for additional connections. In the preferred embodiment, air flow conduit 280 incorporates a quick disconnect coupling 281 that allows the rapid separation of the blower box from the balance of the system. Electrical power cord 292 provides the necessary AC power to drive all of the electrical and electronic components of the system of the present invention.

Also shown in FIG. 16 is wireless data communication device 296 that may be configured to communicate by close proximity (low power) RF signals with the various controller devices incorporated into the system. Recognizing that various calibrations, regimens, parameter settings and the like may need to be programmed into the micro-controllers of the present system, it is beneficial to utilize such close proximity data communication devices to provide a means for modifying the setting of the various controllers. The PC boards described in association with the controller enclosures shown in FIGS. 8 and 9 may incorporate the necessary wireless communication transceiver circuitry to permit such data transmission back and forth with a close proximity handheld unit. The network protocol utilized in the preferred embodiment of the present invention (CAN protocol) may be further utilized with the wireless capability by making the hand held unit a discretely identified node on the network. The hand held unit may then act to reset the parameters programmed into the individual controllers, and/or may act to receive and download historical data associated with the performance of the controller over time in response to the various pressure and temperature changes being monitored as well as the cushion displacement measurements made by the IR sensors.

Although the present invention has been described in terms of the foregoing preferred embodiments, this description has been provided by way of explanation only, and is not intended to be construed as a limitation of the invention. Those skilled in the art will recognize modifications of the present invention that might accommodate specific existing patient support structures or hospital bed configurations. Such modifications as to size, and even configuration, where such modifications are merely coincidental to existing structures of the bed, do not depart from the spirit and scope of the invention.

What is claimed:

1. An apparatus, comprising:
   an inflatable chamber;
   a light transmitter positioned proximal a surface of the inflatable chamber;
   a light receiver positioned proximal the surface of the inflatable chamber;
   a valve controller having controller area network (CAN) circuitry positioned proximal the inflatable chamber and in communication with the light transmitter and the light receiver; and wherein a portion of the inflatable chamber includes a sensor window.

2. The apparatus of claim 1, wherein the inflatable chamber includes an air permeable portion.

3. The apparatus of claim 1, wherein portions of internal surfaces of the inflatable chamber include light reflective properties.

4. The apparatus of claim 1, including a source of pressurized fluid in communication with the valve controller, the source operable to control inflation of the inflatable chamber according to data received by the receiver.

5. An apparatus, comprising:
   an inflatable chamber to support a patient thereon, the inflatable chamber having a reflective internal portion and a sensor window;
   an infra red transmitter positioned proximal the sensor window;
   an infra red receiver positioned proximal the sensor window; and
   a microcontroller having controller area network (CAN) circuitry, the microcontroller in communication with the infra red transmitter and the infra red receiver.

6. The apparatus of claim 5, wherein the inflatable chamber includes a number of internal surfaces defining a number of internal passages.

7. The apparatus of claim 5, wherein the reflective internal portion of the inflatable chamber can include at least a portion of a surface of a passage within the inflatable chamber.

* * * * *